United States Patent [19]

Gibson et al.

[11] Patent Number: 5,533,399

[45] Date of Patent: Jul. 9, 1996

[54] METHOD AND APPARATUS FOR NON-DESTRUCTIVE MEASUREMENT OF ELASTIC PROPERTIES OF STRUCTURAL MATERIALS

[75] Inventors: Ronald F. Gibson; Emmanuel O. Ayorinde, both of Southfield, Mich.

[73] Assignee: Wayne State University, Detroit, Mich.

[21] Appl. No.: 305,402

[22] Filed: Sep. 13, 1994

Related U.S. Application Data

[63] Continuation of Ser. No. 953,896, Sep. 30, 1992, abandoned.

[51] Int. Cl.$^6$ .................................................. G01H 13/00
[52] U.S. Cl. ............................................... 73/579; 73/659
[58] Field of Search ............................ 73/579, 581, 582, 73/602, 584, 658, 659

[56] References Cited

U.S. PATENT DOCUMENTS

| | | | |
|---|---|---|---|
| 4,342,229 | 8/1982 | Massa | 73/579 |
| 4,412,452 | 11/1983 | Biot et al. | 73/579 |
| 4,692,615 | 9/1987 | Mensah et al. | |
| 4,722,223 | 2/1988 | Bach et al. | 73/579 |
| 5,150,617 | 9/1992 | Schwarz et al. | 73/579 |
| 5,269,181 | 12/1994 | Gibson et al. | 73/579 |

FOREIGN PATENT DOCUMENTS 63-250548  10/1988  Japan ...................... 73/579

OTHER PUBLICATIONS

James, D. W., Apparatus for Determining Dynamic Modulus of Elasticity And Internal Damping Capacity.

Date paper of "Durability of Polymer Based Composite Systems for Structural Applications".

L. R. Deobald & R. F. Gibson "Determination of Elastic Constants of Orthotropic Plates by a Modal Analysis/Rayleigh–Ritz Technique", Journal of Sound and Vibration (1988).

W. P. DeWilde et al "Determination of the Material Constants of an Anisotropic Lamina by Free Vibration Analysis", Proceedings of Second International Modal Analysis Conference, Orlando, Floria, I, 44–49 (1984).

H. Sol, et al "Durability of Polymer Based Composite Systems for Structural Applications", ANALATOM Inc., THE RESONALYSER (an article published on durability of polymer based composite systems for structural applications; requires preliminary tests on strips).

J. A. Wolf, Jr. & T. G. Came "Identification of the Elastic Constants for Composites Using Modal Analysis", Society for Experimental Stress Analysis, SESA Spring Meeting (1979).

"Test Procedures for Automotive Structural Composite Materials" Automotive Composites Consortium Materials Work Group (Jan. 1990).

"Improved Approximate Expressions for the Natural Frequencies of Isotropic & Orthotropic Rectangular Plates", Journal of Sound and Vibration, Academic Press Inc (London) (1985).

Primary Examiner—Hezron E. Williams
Assistant Examiner—Nashmiya Ashraf
Attorney, Agent, or Firm—Brooks & Kushman

[57] ABSTRACT

Method and apparatus for deriving four independent elastic constants (longitudinal and transverse Young's moduli, inplane shear modulus and major Poisson's ratio) of composite materials from the modal resonance data of a freely-supported rectangular thin plate made from the material. The method includes the steps of: suspending a panel of the material from a rigid support by a plurality of filaments having a low support stiffness which has minimal effect on motion of the panel; providing a vibration sensor to detect a vibration response in the panel; imparting an impulse to the panel; generating a response signal proportionate to the response in the panel to the impulse imparted; generating an excitation signal in proportion to the impulse; communicating the signals to an analyzer for transforming the signals into a frequency domain; deriving resonance frequencies and associated mode shape indices of the panel; communicating the resonance frequencies and the mode shape indices to a computing device; and predicting and displaying the elastic constants using the computing device.

9 Claims, 4 Drawing Sheets fig-1 fig-2 fig-3 fig-4 fig-5 fig-6 ured 5,533,399

METHOD AND APPARATUS FOR NON-DESTRUCTIVE MEASUREMENT OF ELASTIC PROPERTIES OF STRUCTURAL MATERIALS

This is a continuation of copending application Ser. No. 07/953,896 filed on Sep. 30, 1992 now abandoned.

TECHNICAL FIELD

This invention relates to non-destructive measurement of elastic properties of structural materials. More specifically, the invention relates to a method and apparatus for rapidly obtaining the elastic constants of such materials from plate vibration tests.

BACKGROUND ART

Structural materials may generally be classified as traditional materials or advanced composites. Whether traditional or advanced, it is important that methods be developed for reliably establishing their elastic properties. Such data are necessary for design, quality control, and in-service evaluation. The determination of elastic properties is more difficult for advanced composites than for traditional materials because traditional materials tend to be homogeneous and isotropic, while composites tend to be non-homogeneous and anisotropic. The isotropic material can be considered as a special case of the more general anisotropic material.

The most widely used composite materials are made of polymer resins reinforced with high strength, high stiffness fibers. Experience has shown that many thin, laminated composite plates, shells and panel structures are essentially orthotropic. Orthotropic materials have three mutually perpendicular planes of material property symmetry. However, some composites are comprised of randomly distributed fibers that result in in-plane properties which are nearly isotropic. That is, all planes are planes of material property symmetry.

The elastic behavior of thin orthotropic composite panels may be adequately described by four elastic constants—the longitudinal Young's modulus, $E_x$; the transverse Young's modulus, $E_y$; the in-plane shear modulus, $G_{xy}$; and the major Poisson's ratio, $V_{xy}$. Isotropic composites may be characterized by such elastic constants as the Young's Modulus, E; and the shear modulus, G.

Presently, a number of standards stipulate methods for measurement of the elastic constants of fiber composites. Among these are the standards for high modulus composites drawn up by the ASTM (1987). Some industrial standards also exist. For example, the three major United States automotive manufacturers have developed special standards for automotive composites (Automotive Composites Consortium, 1990). All these methods are based on static tests. They share the major drawback of involving many samples and require special test fixtures. These methods are consequently slow and expensive.

Against this background, it would be desirable to have a test method that would be useful for quickly and continuously monitoring and controlling the quality of composite components.

Some attempts to derive elastic constants have been based on vibration response data. The present invention, however, differs from previous approaches both in the vibrational deflection approximation and the methodology of obtaining optimum values of the desired elastic constants once the vibrational frequency equation is obtained.

SUMMARY OF THE INVENTION

An objective of this invention is to develop a reasonably fast method for measuring all relevant elastic constants of structural materials.

In carrying out the above objective and other objectives and features of the invention, a method is disclosed for determining the elastic properties of a structural material. The method comprises the steps of: suspending the material from a rigid support by filaments which have minimal effect on motion of the material; providing a vibration sensor to detect a vibration response in the material; imparting an impulse to the material; generating a response signal proportionate to the response of the material to the impulse imparted; generating an excitation signal in proportion to the impulse; communicating the signals to an analyzer for transforming the signals into the frequency domain; deriving resonance frequencies; deriving mode shape indices; communicating the resonance frequencies and the mode shape indices to a computing means; and predicting and displaying the elastic constants using the computing means.

An apparatus is disclosed for determining the elastic properties of a thin orthotropic material and a thin isotropic composite material non-destructively. The apparatus comprises a rigid support and a suspending medium extending from the support, the suspending medium engaging the material so that its edges are free of restraint by the suspending medium. An impulse means is provided for imparting an impulse to the material. Connected to the impulse means is a force transducer. The method also includes provision of a vibration sensor for detecting response in the material as a result of the impulse imparted and for generating a signal in proportion thereto. A spectrum analyzer is connected to the vibration sensor for transforming the signal into the frequency domain and obtaining resonance frequencies and modal shape indices. A computing means is disposed in communication with the analyzer for computing from the resonance frequencies and the modal shape indices the elastic constants and for displaying said constants.

BRIEF DESCRIPTION OF THE DRAWINGS

FIG. 5 is a graph showing an equation residual from vibration test data of a square unidirectional E-glass/vinylester plate, which is another example of an advanced composite; and FIG. 6 is a graph showing an equation residual from vibration test data of a rectangular graphite/epoxy plate with a different aspect ratio from the specimen of FIG. 4.

BEST MODE FOR CARRYING OUT THE INVENTION

The present invention primarily addresses the derivation of elastic properties from vibration frequencies and mode shapes. Every structure, whether or not orthotropic, has its natural frequencies of vibration in response to a given stimulus. While vibrating at any of these frequencies, the structure assumes a profile, known as a mode shape, which is peculiar to that frequency.

Orthotropic Material

In an orthotropic material, there are three mutually perpendicular planes of material property symmetry. Before discussing the process of deriving elastic properties from vibration frequencies, this disclosure will first consider the determination of frequencies from data concerning elastic properties.

The partial differential equation governing the free transverse vibration of a symmetrically laminated thin orthotropic plate at equilibrium in the x-y plane may conventionally be written as $$D_{11}\frac{\partial^4 w}{\partial x^4} + 4D_{16}\frac{\partial^4 w}{\partial x^3 \partial y} + 2(D_{12}+2D_{66})\frac{\partial^4 w}{\partial x^2 \partial y^2} + \qquad(1)$$

$$4D_{26}\frac{\partial^4 w}{\partial x \partial y^3} + D_{22}\frac{\partial^4 w}{\partial y^4} + \rho h \frac{\partial^2 w}{\partial t^2} = 0$$

where x and y are the orthogonal plane coordinates, the plate deflection $w=w(x,y,t)$, the $D_{ij}$'s are the volume averaged bending stiffnesses of classical lamination theory (CLT), $\rho$ is the volume averaged plate density, or mass per unit volume, h is the average plate thickness and t represents time. While averaged values are used throughout this disclosure, the technique may be extended to the determination of property distribution in non-homogeneous components.

The deflection amplitude W may conventionally be approximately represented by the series $$W(x,y) = \sum_{i=1}^{m}\sum_{j=1}^{n} A_{ij}\theta_i(x)\phi_j(y) \qquad(2)$$

where $A_{ij}$ are undetermined constants and $\theta_i(x)$ and $\phi_j(y)$ are admissible characteristic normal-mode beam functions in the appropriate directions. It may be alternatively represented by $$W(x,y) = \sum_{i=1}^{k} B_i \psi_i(x,y) \qquad(3)$$

where $B_i$ are undetermined constants and $\psi_i(x,y)$ are admissible characteristic plate functions.

The energy method, in various forms, is the most widely used approximate analysis procedure. Accordingly, the expressions for the maximum potential and kinetic energies of a harmonically vibrating, generally orthotropic plate may conventionally be respectively rendered as $$V_{max} = \frac{1}{2}\int_0^a\int_0^b \left[ D_{11}\left(\frac{\partial^2 W}{\partial x^2}\right)^2 + 2D_{12}\frac{\partial^2 W}{\partial x^2}\frac{\partial^2 W}{\partial y^2} + \right. \qquad(4)$$

$$D_{22}\left(\frac{\partial^2 W}{\partial y^2}\right)^2 + 4D_{66}\left(\frac{\partial^2 W}{\partial x \partial y}\right)^2 + 4D_{16}\frac{\partial^2 W}{\partial x^2}\frac{\partial^2 W}{\partial x \partial y} +$$

$$\left. 4D_{26}\frac{\partial^2 W}{\partial y^2}\frac{\partial^2 W}{\partial x \partial y} \right] dydx$$

and $$T_{max} = \frac{1}{2}\rho h\omega^2 \int_0^a\int_0^b W^2 dydx \qquad(5)$$

where $\omega$ is the frequency of vibration, and a and b are the plate side dimensions along the x- and y- axes respectively.

In specially orthotropic materials, the coordinate axes used to describe the material properties are selected so as to coincide with the axes of material symmetry. For specially orthotropic plates, Equations (1) and (4) become simpler, as $D_{16}=D_{26}=0$, $D_{11}=D_x$, $D_{22}=D_y$, $D_{12}=V_{xy}D_y$ and $D_{66}=D_{xy}$. In all of these equations $D_x=E_x h^3/12(1-V_{xy}V_{yx})$ $D_y=E_y D_x/E_x$, $D_{xy}=h^3 G_{xy}/12$, $E_x$ and $E_y$ are Young's moduli in the x- and y- directions respectively, $G_{xy}$ is the shear modulus associated with the x-y plane, and $V_{xy}$ and $V_{yx}$ are the major and minor Poisson's ratios, respectively.

The next step in the process of estimating frequencies from property data is to substitute the assumed deflection expression of Equation (3) into the energy expressions of Equations (4) and (5) and equate the maxima of the potential and kinetic energies according to the known Rayleigh method. This yields the frequency $\omega$. The Rayleigh method is one of several energy methods. Others could be used.

An improved Rayleigh method is disclosed by C. S. Kim and S. M. Dickinson in a paper entitled "Improved Approximate Expressions For The Natural Frequencies Of Isotropic And Orthotropic Rectangular Plates", JOURNAL OF SOUND AND VIBRATION, Vol. 103, No. 1, 1985, pp. 142-149. But that method has only been used to obtain frequencies from property data and consists of applying the principle of minimum potential energy to obtain an optimized three-term deflection representation. The resulting expression is given in the following equation and may be qualitatively conceived as an optimal combination of the mode of interest (i.e. the resonance mode whose experimental data is being fitted to the frequency equation) and the next two higher modes:

$$W(x,y) \sim A\{\theta_i(x)\ \psi(y) - c\ \theta_i(x)\ \psi_m(y) - d\ \theta_m(x)\ \psi_j(y)\} \qquad(6)$$

Here, the mode shape of interest is the (i,j)th, A is a constant, $\theta_i(x)$ and $\phi_j(y)$ are the appropriate $i^{th}$ and $j^{th}$ beam mode shapes, $m=i+1$, $n=j+1$ for dissimilar beam end conditions, and $m=i+2$, $n=j+2$ for the case where the conditions are the same at each end. Constants c and d are obtained by optimizing the frequency using the principle of minimum potential energy (i.e. $\partial V_{max}/\partial c=0$ and $\partial V_{max}/\partial d=0$).

Since this approach leads to a much simpler frequency expression, it is particularly adaptable to the prediction of frequencies from property data. The present invention involves a novel application of this improved Rayleigh method to infer elastic properties from frequency data.

Although, as will be seen later, results obtained by using this three-term expression for W are quite reasonable, it is envisaged that one possible future improvement of our procedure is to use additional terms in the expression for W for increased accuracy.

For specially orthotropic rectangular plates, Equation (4) becomes $$V_{max} = \frac{1}{2}\int_0^a\int_0^b \left[ D_x\left(\frac{\partial^2 W}{\partial x^2}\right)^2 + 2v_{xy}D_y\frac{\partial^2 W}{\partial x^2}\frac{\partial^2 W}{\partial y^2} + \right. \qquad(7)$$

$$\left. D_y\left(\frac{\partial^2 W}{\partial y^2}\right)^2 + 4D_{xy}\left(\frac{\partial^2 W}{\partial x \partial y}\right)^2 \right] dydx$$

and Equation (5) remains the same.

By minimizing the potential energy in Equation (7) with respect to the constants c and d, respectively, in the deflection function of Equation (6), previous investigators have obtained $$c = (C_{mj}E_{ij} - E_{ij}F)/(C_{in}C_{mj} - F^2) \quad d = (C_{in}E_{ji} - E_{ij}F)/(C_{in}C_{mj} - F^2) \quad (8)$$

where $$C_{ij} = (D_x/H)G_i^4(b^2/a^2) = (D_y/H)G_j^4(a^2/b^2) + 2\{H_iH_j + 2(D_{xy}/H)(J_iJ_j - J_iH_j)\}$$

$$E_{ij} = H_i(K_j + L_j)\{2(D_{xy}/H) - 1\} + 4(D_{xy}/H)J_iM_j$$

$$E_{ji} = H_j(K_i + L_i)\{2(D_{xy}/H) - 1\} + 4(D_{xy}/H)J_jM_i$$

$$F = -(K_iK_j + L_iL_j)\{2(D_{xy}/H) - 1\} + 4(D_{xy}/H)M_iM_j$$

and the integrals $G_i$, $H_i$, $J_i$, $K_i$, $L_i$, and $M_i$, which are based on normal-mode beam characteristic functions, are given by $$G_i^4 = (a^4/\pi^4) \int_0^a \left(\frac{\partial^2 \theta_i}{\partial x^2}\right)^2 dx / \int_0^a (\theta_i)^2 dx \quad (9)$$

$$H_i = -(a^2/\pi^2) \int_0^a \theta_i \frac{\partial^2 \theta_i}{\partial x^2} dx / \int_0^a (\theta_i)^2 dx \quad (10)$$

$$J_i = (a^2/\pi^2) \int_0^a \left(\frac{\partial \theta_i}{\partial x}\right)^2 dx / \int_0^a (\theta_i)^2 dx \quad (11)$$

$$K_i = (a^2/\pi^2) \int_0^a \theta_i \frac{\partial^2 \theta_m}{\partial x^2} dx / \int_0^a (\theta_i)^2 dx \quad (12)$$

$$L_i = (a^2/\pi^2) \int_0^a \frac{\partial^2 \theta_i}{\partial x^2} \theta_m dx / \int_0^a (\theta_i)^2 dx \quad (13)$$

$$M_i = (a^2/\pi^2) \int_0^a \frac{\partial \theta_i}{\partial x} \frac{\partial \theta_m}{\partial x} dx / \int_0^a (\theta_i)^2 dx \quad (14)$$

and $$H = v_{xy}D_y + 2D_{xy} \quad (15)$$

When the maximum values of the kinetic and potential energies (Equations (5) and (7)) are equated according to Rayleigh's method, the frequency equation obtained is $$\frac{\rho h a^2 b^2}{\pi^4 H} \omega^2 = \frac{C_{ij} + c^2 C_{in} + d^2 C_{mj} - 2cE_{ij} - 2dE_{ji} + 2cdF}{1 + c^2 + d^2} \quad (16)$$

Previous investigators have used this equation to solve for frequencies based on input data for material properties.

The more difficult problem to which the present invention is directed, however, involves the solution for properties based on measured frequency data. For such purposes, it is better to rearrange Equation (16) as:

$$\frac{\rho h a^2 b^2}{\pi^4} = \frac{H(C_{ij} + C^2 C_{in} + d^2 C_{mj} - 2cE_{ij} - 2dE_{ji} + 2cdF)}{\omega^2(1 + c^2 + d^2)} \quad (17)$$

The reason for this preference is that in the latter form, the left hand side (LHS) is completely determined by the mass density and geometry of a given plate. Unlike the right hand side (RHS), the LHS is totally independent of modal frequencies and indices as well as elastic material constants. The LHS may therefore be taken as a benchmark against which changing RHS values may be compared as they are determined from different experimental modal parameters and trial values of the elastic constants.

In this regard, Equation (17) may be essentially written as $$f_L = f_R \quad (18)$$

If we know exactly the resonance frequency $\omega$ and the four elastic constants, then Equation (18) will be exactly satisfied. However, since this is not the case, the equation can only be approximately satisfied for each frequency. Thus, for any measured frequency, we may say $f_R - f_L$ is equal to a residual, and define a dimensionless residual, $\delta$, as $$\frac{f_R}{f_L} - 1 = \delta \quad (19)$$

This dimensionless form is preferable here and is essential in other cases when the objective function (to be defined later) involves additional contributions. In particular, for one mode set (i.e. four modal frequencies and their corresponding modal shape indices, from which we can extract estimates of the four unknown elastic constants), we have $$\frac{f_{R_i}}{f_L} - 1 = \delta_i \quad (20)$$

$$i = 1, 2, 3, 4$$

Since $\delta_i$ may be positive or negative, its square is chosen as a measure of how accurately the frequency Equation (16) is satisfied for the frequency value. Thus, a good measure of how well the four frequencies and the trial values of the elastic constants together satisfy the frequency equation should be indicated by the sum of squares of the four appropriate $\delta_i$ values. The residual corresponding to the frequency equation satisfaction, $R_Q$, is therefore the objective function that needs to be minimized. It is given by $$R_Q = \sum_{i=1}^{4} \delta_i^2 \quad (21)$$

where the subscript Q denotes "equation".

The resulting set of frequency equations can be solved in many ways. Direct solution of the resulting matrix equation using inversion is possible. However, significant variations in the magnitudes of the elements tend to make some of the matrices ill-conditioned, hence incapable of yielding acceptable results. Solutions by the finite-element and finite-difference methods are also possible, but would be much more computationally costly, although such methods could be considered for full three-dimensional analysis.

Even with the regression method used here, several options are possible, and many were tried, although the present invention is based on the use of only the objective function of Equation (21).

More general objective functions could be formed in various ways. It is well known that experimental vibration response data are subject to error. Assume that one of the known plate parameters p, a, b, h (i.e. mass density, major and minor dimensions, and overall thickness) is in fact unknown. Then we may utilize a set of experimental vibration response data and trial values of the elastic constants to solve the frequency equations for the parameter. Its computed value would, in general, be different from its actual value.

Thus, in addition to the degree of accuracy with which a particular set of data (vibration response data and elastic constants) satisfies the governing equations, similar measures of how well it predicts each of the four known plate parameters could be used as contributing objective functions. The implication is that a completely correct set of vibration response and elastic data would exactly satisfy the equations and would also accurately "predict" those parameters.

The dimensionless residual contributed by the estimate of an individual parameter would therefore be $$\delta_\kappa = \left( \frac{\text{computed value of parameter } \kappa}{\text{actual value of parameter } \kappa} - 1 \right) \quad (22)$$

Thus, an expanded objective function may be defined as $$O.F. = R_Q + R_P + R_a + R_b + R_h \quad (23)$$

where a typical residual $R_k$ is given by $$R_\kappa = \sum_{i=1}^{4} \delta_\kappa^2 \quad (24)$$

In Equation (24), i is summed over the four modes that are always required to extract the four elastic constants, and K represents any of Q, ρ, a, b, and h as detailed in Equation (23). It is also conceivable that, owing to some peculiar behavior of an advanced composite material, the proper effects of the various contributions in Equation (23) may not be uniform. A more general objective function would therefore include weighting functions $C_K$, as $$O.F. = C_Q R_Q + C_p R_p + C_a R_a + C_b R_b + C_h R_h \quad (25)$$

The determination of appropriate weights could be done semi-empirically using data from known cases. From the large number of options tried, it was found that for some optimization schemes, in certain circumstances, the weighting pattern significantly affects the convergence speed and accuracy of computations. However, only the objective function of Equation (21) was used to obtain the results disclosed herein. This is equivalent to setting $C_Q=1$ and $C_p=C_a=C_b=C_h=0$ in Equation (25).

Isotropic Material

If the material is isotropic or almost isotropic, its properties are essentially the same in all directions. For such materials, only two elastic constants are generally sought. In such cases, two frequency equations are sufficient. Accuracy is improved when more data are used. The full program for an orthotropic material as discussed above can be used as it stands. Alternatively, it can be adapted for the case of isotropy, in which case the program yields results more quickly.

For isotropic materials, the method used to search for an optimal set of solutions calls for the objective function to be the residual based on the mean-square deviations of the predicted E value. Such values are obtained by using test data from different sets of four modes at a time.

The equation residual therefore becomes $$R_Q = \sum_{i=1}^{4} (E_i - E_m)^2 \quad (26)$$

where $$E_m = 0.25\{\Sigma(E_i)^2\} \quad (27)$$

Experimental and Computational Procedures

Previously obtained experimental vibration data for 254 mm-square aluminum and graphite/epoxy plates were reported by L. R. Deobald and R. F. Gibson in a paper entitled "Determination Of Elastic Constants Of Orthotropic Plates By A Modal Analysis/Rayleigh-Ritz Technique" JOURNAL OF SOUND AND VIBRATION, Vol. 124, No 2, 1988, pp. 269–283. Such data were used to validate the analysis disclosed herein. In addition, a unidirectional E-glass/vinylester (FRP 470) plate 179.4 mm×165.9 mm and a 12-ply unidirectional graphite/epoxy plate 255.6 mm×126.2 mm were tested in the apparatus of FIG. 1. Their vibration response frequencies and mode shapes were established. The plate suspension apparatus of FIG. 1 differs from earlier work, in which the plate was placed on a soft cotton pad to simulate free support.

In the present invention (see, e.g. FIG. 1), the plate is suspended by suspending media, such as filaments 14 made, for example, of nylon, in an inverted "Y" arrangement 30, which has extremely low vertical impedance.

Figure 1:
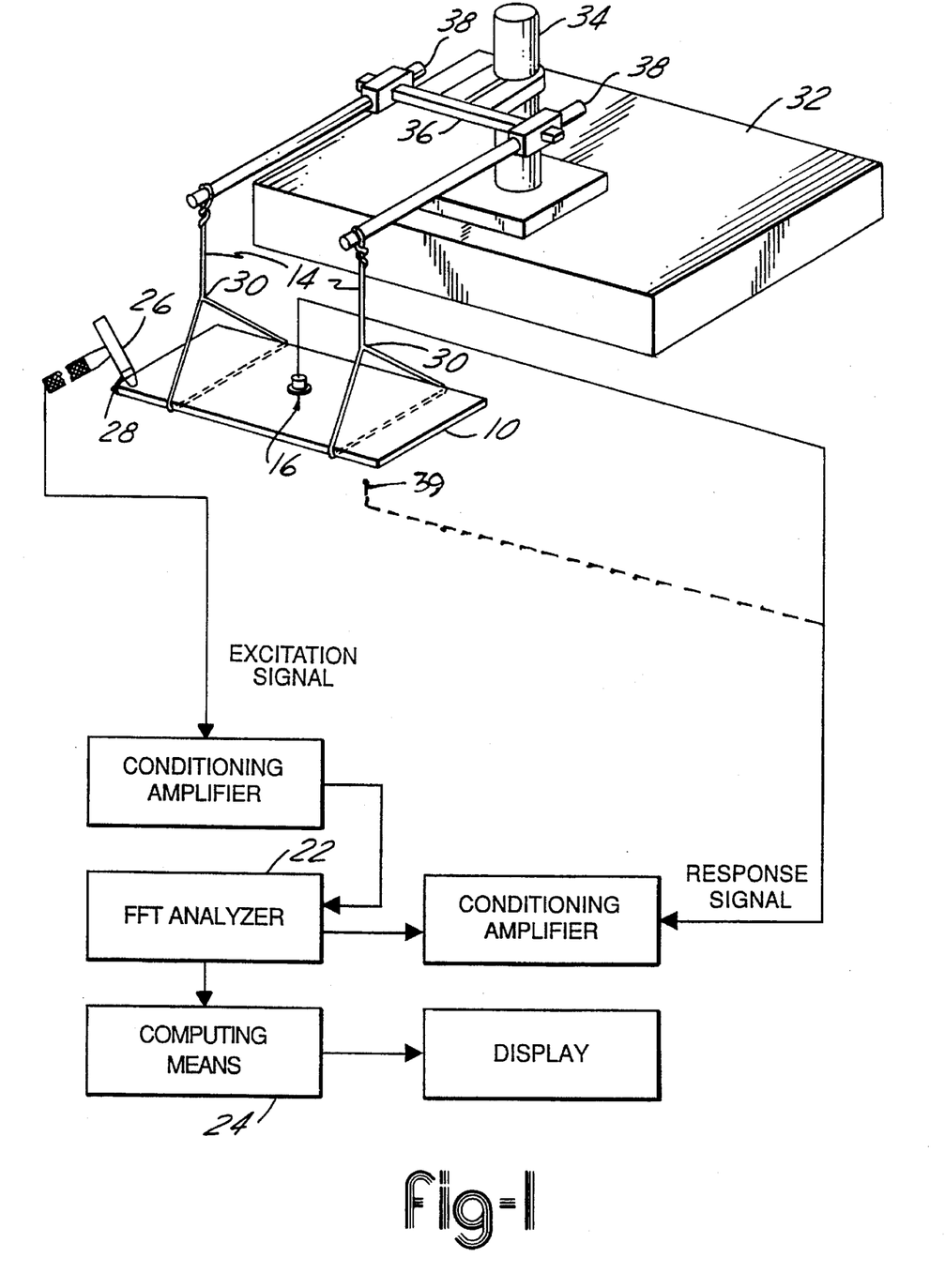
FIG. 1 is a perspective view of an apparatus used to determine the elastic constants of structural materials, including a block diagram depicting the vibration test apparatus used herein.

A miniature piezoelectric accelerometer is used as a vibration sensor 16. A robust steel stand 34 with a welded steel cross-piece 36 is firmly clamped onto a vibration table 32. Two stiff cantilever bars 38 are clamped to each end of the cross-bar 36, thereby providing a means for suspending a test plate 10 of the material from the filaments 14. The vibration sensor may, if desired, comprise a non-contacting eddy-current probe 39 (FIG. 1).

Care is taken in the choice of dimensions and clamping of the stand 34 to ensure that its resonances do not interfere with those of the plate 10. This was verified by testing with an accelerometer placed on the tips of the cantilevers 38. Lack of any measurable response confirmed that the support system was sufficiently stiff.

Experimental vibration analysis is carried out by an impulse method, which is convenient and fast. An impulse means such as hammer 26 is instrumented with a piezoelectric force transducer 28 (such as the PCB Model 208 A02) in its tip and is used to deliver sharp impacts to the plate. A miniature accelerometer 16 (such as the PCB Model 303 A03) is mounted with beeswax on the plate 10 to detect a response signal. This signal is conducted via a conditioning amplifier (such as the PCB Model 480A) to a spectrum (FFT) analyzer 22 (such as the Hewlett-Packard Model 3582A) for transformation into the frequency domain.

The analyzer 22 has a zoom feature which is used to accurately obtain resonance frequencies. In each test, several combinations of excitation and response locations were used to ensure that the resonances were clearly obtained. In the case of the rectangular graphite-epoxy plate, a second vibration test was conducted with the plate 10 on a cotton pad for comparison. The dimensions of the sheet-molding compound (SMC) plate were 306 mm×305.6 mm×2.682 mm. Those of the rectangular graphite-epoxy plate were 255.6 mm×286.2 mm×1.753 mm.

The SMC comprises randomly-oriented, chopped glass fibers in a polyester matrix. The graphite/epoxy plates in all cases consisted of 12 plies at 0° orientation. The modal frequencies were located by impacting the plate at many points and using the zoom feature of the analyzer 22. The mode shapes corresponding to these resonance frequencies were determined by using the impulse hammer 26 to locate the nodal lines responsible for the subtraction of a particular mode from the spectrum. Using the convention of numbers of halfwaves along (or alternatively, nodal lines perpendicular to) each principal direction, gave the required modal shape indices.

The modal shape indices and corresponding frequencies are utilized as inputs to a computing means 24 including a program. Though such inputs may be made manually, computerized data acquisition techniques may also be used. In such techniques, the vibration sensors 16 provide input signals to one or more analog-to-digital convertors, which, in turn, provide digital data to the computer 24. In the program, a search is carried out in the four-space of the parameters $E_x$, $E_y$, $G_{xy}$, and $V_{xy}$. The residual of Equation (21) was used as the objective function to be minimized.

Figure 2:
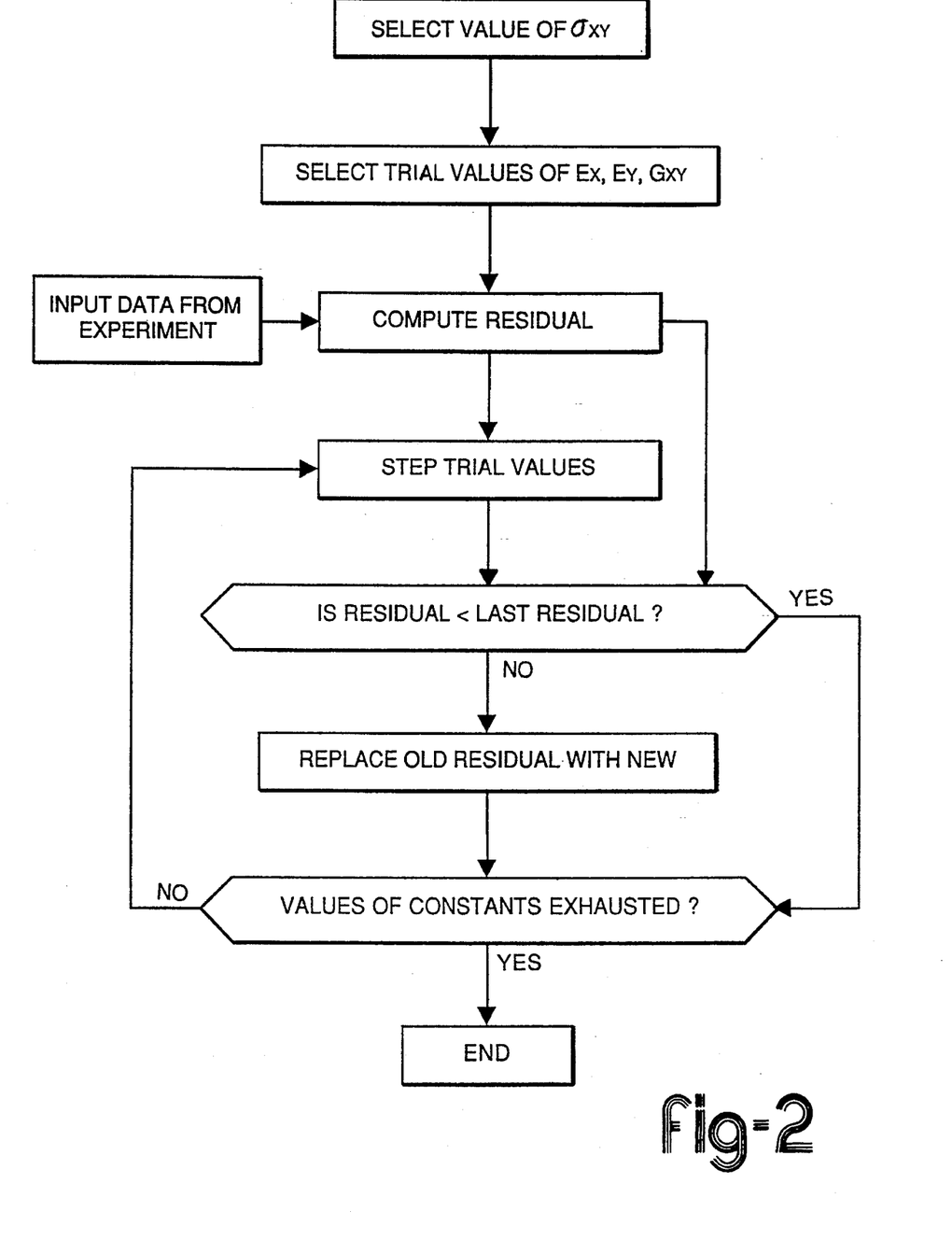
FIG. 2 is a flow chart for determining elastic moduli.
Figure 3:
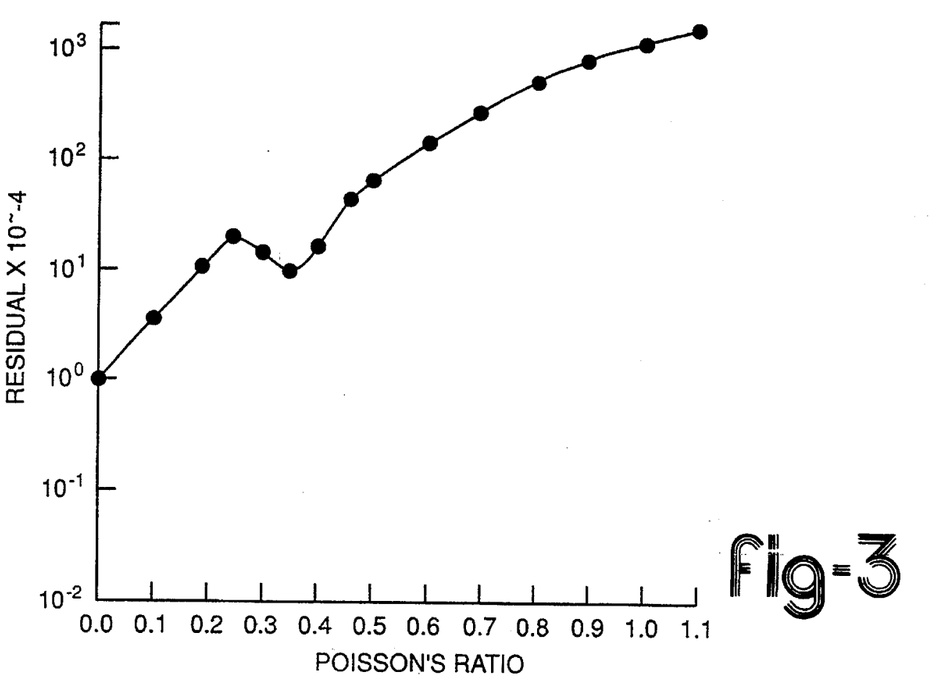
FIG. 3 is a graph showing an equation residual from vibration test data of a square aluminum plate, which is representative of a traditional isotropic material.
Figure 4:
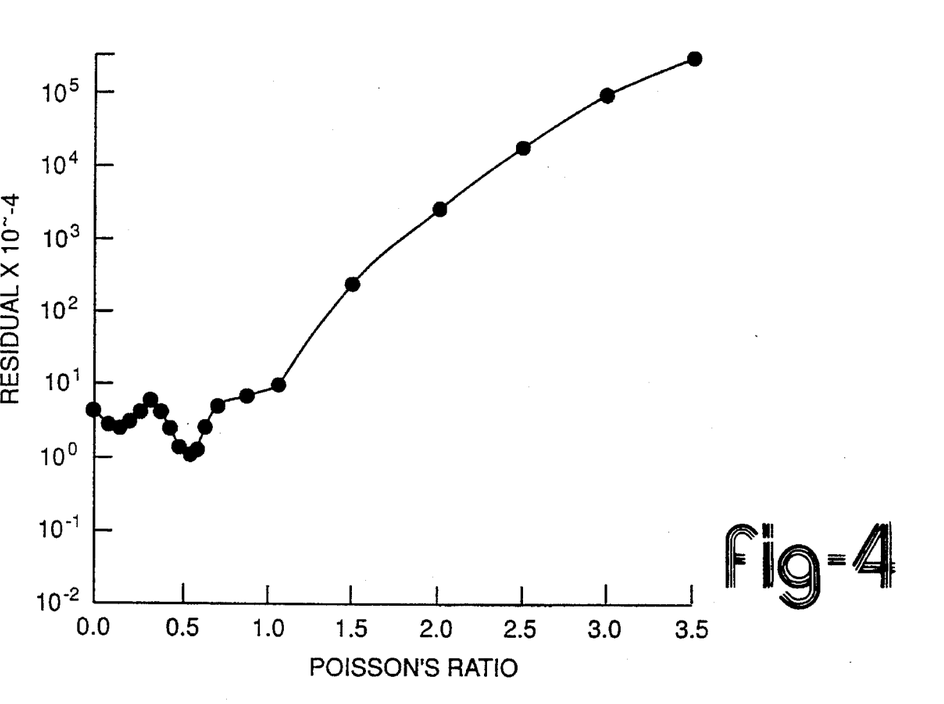
FIG. 4 is a graph showing an equation residual from vibration test data of a square graphite/epoxy plate, which is representative of advanced composites.

The flow chart of FIG. 2 indicates the logical structure of the program which is operational in the computer 24. Since it was discovered that the Poisson's ratio seemed to be largely responsible for the high modal density of the four-parameter objective function, an alternative of optimizing that function in the $E_x$-$E_y$-$G_{xy}$ space for specific values of Poisson's ratio was employed. The results presented in FIGS. 3–6 are from this latter approach. The Poisson's ratio was searched up to the upper theoretical minimum given by $(E_x/E_y)^{1/4}$. A typical computation time for a cycle on a 386-type personal computer was under 6 minutes.

Results and Discussion

Tables 1(a) and 1(b) show the plate frequencies obtained experimentally and computed by three different methods, for aluminum and graphite/epoxy respectively.

Tables 2(a) and 2(b) show the results from the current prediction of the elastic constants for a square SMC and for a rectangular graphite/epoxy plate, respectively.

Tables 3(a) and 3(b) show the elastic constants predicted from the isotropic assumption for aluminum and SMC respectively.

Table 4 lists the elastic constants of graphite/epoxy as obtained from a square plate suspended by nylon filaments 14, a rectangular plate similarly suspended, and the same rectangular plate cushioned on a cotton wool pad.

FIGS. 3–6 show the residual plots for square aluminum, square graphite-epoxy, square SMC and rectangular graphite-epoxy plates, respectively.

The values of plate resonance frequencies predicted by the finite-element, 36-term Rayleigh-Ritz and the optimized 3-mode Rayleigh method used in our solution are shown to be favorably comparable to the experimental values in Tables 1(a) and 1(b), respectively. On the basis of the good agreement between actual and predicted frequencies inferred from elastic properties, the present disclosure demonstrates that elastic properties may be inferred from observed vibrational characteristics.

The limitation of using only three modes (however optimized) to represent a theoretically infinite series can, of course, only be removed by including more terms. The results of such an extension to six terms is the subject of later work.

The results of Table 2(a) show that the full orthotropic program also reasonably predicts the elastic properties of SMC. Although theoretically expected to be isotropic due to random fiber orientation, the peculiarities of mold flow during preparation actually includes most samples with slightly anisotropic characteristics.

This phenomenon is believed to have accentuated the difference between the predicted values of $E_x$ and $E_y$. Only E (taken as $E_x$) and were supplied by the manufacturer. The "actual" values of $G_{xy}$ and $E_y$ were computed on the basis of assumed isotropy.

Table 2(b) shows that the values of elastic constants predicted from a rectangular, highly-orthotropic (graphite/epoxy) plate tested on a cotton pad tend to be inaccurate.

The summary given in Table 4 shows this even more clearly. It may be concluded from the results in this latter table that the cotton pad support is quite inferior to the nylon filament suspension 14. This is not surprising, since the vertical impedance from the cotton pad could be expected to be significantly more than that of the nylon filament suspension 14. The damping loss factors measured for the cotton pad support were 10 to 100 times higher than those for the nylon filament suspension 14. In addition, measurement reproducibility was found to be much better for the nylon filament suspension 14.

The use of the isotropic version of the program is worthwhile. In cases where it is applicable, this is shown in Tables 3(a) and 3(b) for aluminum and SMC, respectively. Since this program obtains the results in under 1 minute on a 386 computer using QuickBasic, its use represents a speedy attempt at estimating the elastic constants.

Detailed examination of the behavior of the equation residual, such as those shown in FIGS. 3–6, shows that the first turning-point minimum in such plots appears to yield the optimum values of all four constants. Other minima, when present, yield elastic constants that deviate more from the correct values.

The method of quickly extracting the four independent elastic constants of orthotropic materials from plate vibration test data has been successfully applied to an isotropic, a nearly isotropic, a moderately orthotropic, and a highly orthotropic material. The method has been extended in theory to the case of initially-assumed isotropy, and the validity of this extension is verified by two cases. The basic method has also been used to investigate the effects of support conditions on the values of the predicted elastic constants. The method is presently based on the classical lamination theory (CLT) and an optimized three-mode Rayleigh formulation for the plate vibration model. However, the method is capable of better accuracy by taking additional terms on the right hand side of Equation (6) above, or by applying a higher-order theory, including shear terms.

The present method and the foregoing discussion apply to thin plates for which through-the-thickness shear and rotary inertia may be neglected. However, thick composite plates are often required for various applications. Theories more refined than the CLT, some of which have been mentioned earlier, are therefore needed. From a detailed assessment of such higher-order theories, it appears that the piecewise-linear individual-layer theory may be the simplest and most effective way to extend the present work to thick plates.

Additionally, the disclosed technique may be used to evaluate composite parts having arbitrary geometry, including full scale components.

Furthermore, the disclosed techniques may be integrated into the manufacturing process in order to control, as well as monitor, the elastic properties of the components. This is accomplished by generating and communicating feedback signals representative of the elastic properties to the processing equipment. In this way, various process control parameters, such as pressure, temperature, and heating and cooling rates may be adjusted to maintain the elastic properties within the desired limits.

Thus, there has been disclosed a method for extracting the elastic constants of orthotropic materials from experimental plate vibration data. The method is adaptable to a wide variety of formulations of the elastic-dynamic behavior of laminated plates.

TABLE 1(a)

Natural Frequencies of Square Aluminum Plate With Completely-Free Boundary Conditions
Natural Frequencies (Hz)

| Modal Indices | Experimental* | SAP IV FEM* | 36-Term* Rayleigh | Optimized 3-Mode |
|---|---|---|---|---|
| 2,2 | 156.7 | 161.4 [3.0] | 163.2 [4.2] | 164.3 [4.8] |
| 2,3 | 411.7 | 412.9 [0.3] | 424.3 [3.1] | 431.0 [4.7] |
| 3,2 | 411.7 | 412.9 [0.3] | 424.3 [3.1] | 431.0 [4.7] |
| 1,4 | 744.9 | 719.3 [−3.4] | 749.4 [0.6] | 750.9 [−0.8] |
| 4,1 | 744.9 | 719.3 [−3.4] | 749.4 [0.6] | 750.9 [−0.8] |
| 3,3 | 755.7 | 755.9 [0.1] | 780.5 [3.3] | 787.2 [4.2] |
| 4,2 | 821.8 | 902.7 [9.8] | 843.4 [2.6] | 902.7 [9.8] |
| 2,4 | 936.5 | 917.6 [−2.0] | 949.8 [1.4] | 902.7 [−3.6] |

*Source: Deobald, L. R. and Gibson, R. F., "Determination Of Elastic Constants Of Orthotropic Plates By A Modal Analysis/Rayleight-Ritz Technique", JOURNAL OF SOUND AND VIBRATION, Vol. 124, No. 2, 1988, pp. 269–283.

TABLE 1(b)

Natural Frequencies Of Square Graphite/Epoxy Plate With Completely-Free Boundary Conditions
Natural Frequencies (Hz)

| Modal Indices | Experimental* | SAP IV FEM* | 36-Term* Rayleigh | Optimized 3-Mode |
|---|---|---|---|---|
| 2,2 | 49.4 | 51.3 [4.0] | 51.8 [4.9] | 52.1 [5.5] |
| 1,3 | 78.9 | 60.5 [−23.0] | 60.2 [−24.0] | 60.3 [−23.6] |
| 2,3 | 113.2 | 120.7 [6.6] | 122.0 [7.8] | 122.5 [8.2] |
| 1,4 | 188.3 | 161.8 [−14.0] | 165.9 [−12.0] | 166.2 [−11.8] |
| 3,1 | 210.5 | 208.6 [−0.9] | 212.7 [1.1] | 212.8 [1.1] |
| 2,4 | 222.4 | 225.2 [1.3] | 229.0 [3.0] | 229.3 [3.1] |
| 3,2 | 231.6 | 231.6 [0.0] | 236.7 [2.2] | 237.2 [2.4] |
| 3,3 | 295.2 | 299.2 [1.4] | 306.5 [3.8] | 308.8 [4.6] |
| 1,5 | 350.0 | 316.2 [−9.7] | 326.1 [−6.8] | 325.7 [−6.9] |
| 2,5 | 381.3 | 378.8 [−0.7] | 380.2 [1.3] | 399.1 [4.7] |

*Source: Deobald, L. R. and Gibson, R. F., "Determination Of Elastic Constants Of Orthotropic Plates By A Modal Analysis/Rayleight-Ritz Technique", JOURNAL OF SOUND AND VIBRATION, Vol. 124, No. 2, 1988, pp. 269–283.

TABLE 2(a)

Elastic Constants Of SMC (RI 9466) From Modal Data Of Square Plate [Modes (1,4), (3,3), (2,4), (1,5), (2,5)]

| Mode Set | Ex (GPa) | Ey (GPa) | Gxy (GPa) | V xy | Residual × $10^4$ |
|---|---|---|---|---|---|
| 1 | 16.59 | 16.55 | 6.09 | 0.24 | 37.56 |
| 2 | 18.19 | 15.47 | 5.79 | 0.29 | 102.58 |
| 3 | 19.73 | 15.66 | 6.40 | 0.24 | 96.57 |
| 4 | 20.97 | 15.62 | 5.67 | 0.24 | 33.67 |
| 5 | 16.43 | 16.19 | 6.14 | 0.10 | 90.92 |
| Weighted Average | 18.61 | 15.96 | 5.98 | 0.23 | |
| Actual | 16.20 | 16.20+ | 6.35+ | 0.275 | |

+means assumed isotropy

TABLE 2(b)

Elastic Constants Of Graphite/Epoxy From Modal Data Of Rectangular Plate Supported on Cotton Pad [Modes (2,2), (3,1), (3,2), (3,3), (4,2); plate aspect ratio 2.05]

| Mode Set | Ex (GPa) | Ey (GPa) | Gxy (GPa) | V xy | Residual × $10^4$ |
|---|---|---|---|---|---|
| 1 | 149.66 | 13.04 | 5.54 | 0.21 | 8.93 |
| 2 | 144.92 | 13.52 | 5.27 | 0.38 | 31.63 |
| 3 | 137.95 | 13.52 | 5.27 | 0.56 | 18.07 |
| 4 | 144.01 | 13.52 | 5.27 | 0.38 | 31.63 |
| 5 | 146.23 | 10.20 | 5.63 | 0+ | 42.40 |
| Weighted Average | 145.43 | 13.29 | 5.40 | 0.34 | |
| Actual | 127.90 | 10.27 | 7.3 | 0.22 | |

+means no proper minimum

TABLE 3(a)

Elastic Properties Of Aluminum Predicted From The Isotropic Assumption [Modes (2,2), (2,3), (3,2), (1,4), (4,1) Of Square Plate]

| Mode Set* | E (GPa) | v |
|---|---|---|
| 1 | 68.10 | 0.368 |
| 2 | 66.59 | 0.408 |
| 3 | 68.49 | 0.372 |
| 4 | 68.49 | 0.372 |
| 5 | 68.10 | 0.368 |
| Average | 67.95 | 0.378 |
| Std. Deviation | 0.79 | 0.017 |
| Actual | 72.4 | 0.33 |

*$i^{th}$ mode set = $i^{th}$ group of 4 modes when given list of 5 modes is arranged in cyclic order.

TABLE 3(b)

Elastic Properties Of SMC (RI 9466) Predicted From The Isotropic Assumption [Modes (1,4), (3,3), (2,4), (1,5), (2,5) of Square Plate]

| Mode Set* | E (GPa) | v |
|---|---|---|
| 1 | 15.63 | 0.285 |
| 2 | 15.41 | 0.285 |
| 3 | 15.82 | 0.209 |
| 4 | 15.10 | 0.285 |
| 5 | 15.41 | 0.260 |
| Average | 15.47 | 0.265 |
| Std. Deviation | 0.27 | 0.033 |
| Actual | 16.20 | 0.275 |

TABLE 4

Elastic Properties Of Graphite Epoxy

| Plate Geometry and Support Type | Ex (GPa) | Ey (GPa) | Gxy (GPa) | V xy |
|---|---|---|---|---|
| Rectangular plate [2.03:1], cotton pad support | 145.4 | 13.3 | 5.4 | 0.34 |
| Rectangular plate [2.03:1], nylon filament support | 140.3 | 10.80 | 6.4 | 0.26 |
| Square plate, nylon filament support | 124.5 | 10.50 | 6.2 | 0.22 |
| Actual* | 127.9 | 10.27 | 7.3 | 0.22 |

*Deobald & Gibson, "Determination of Elastic Constants of Orthotropic Plates By A Modal Analysis/Rayleigh-Ritz Technique", JOURNAL OF SOUND AND VIBRATION, Vol. 124, No. 2, 1988, pp. 269–283.

What is claimed is:

1. A method for determining the elastic properties of either an isotropic or orthotropic structural material, where it is unknown before testing whether the structural material is isotropic or orthotropic, comprising the steps of:

suspending a single plate alone of the material from a rigid support by a plurality of filaments having a low support stiffness and having minimal effect on motion of the material so that the only observations needed for determining the elastic properties are made from the single plate, absent any prior assumptions about elastic constants;

providing a vibration sensor to detect a vibration response in the material;

imparting an impulse to the material;

generating a response signal proportionate to the response in the material to the impulse imparted;

generating an excitation signal in proportion to the impulse;

communicating the response signal to an analyzer for transforming the response signal into a frequency domain;

deriving resonance frequencies and associated mode shape indices of the material;

communicating the resonance frequencies and the mode shape indices to a computing means;

computing and displaying four elastic constants ($E_x$, $E_y$, $G_{xy}$, and $v_{xy}$) using the computing means; and determining after the computing and displaying step that the material is orthotropic or isotropic by inspection of the four elastic constants.

2. A method for determining the elastic properties of a single plate of a thin composite of either isotropic or orthotropic structural material non-destructively where it is unknown before testing whether the structural material is isotropic or orthotropic, comprising the steps of:

suspending the single plate of either an isotropic or orthotropic material from a rigid support by a fine suspending medium so that a small angle is defined between the suspending medium and the material and so that edges of the material are free of appreciable restraint by the suspending medium;

providing a vibration sensor in communication with the material to detect a vibration response;

imparting an impulse to the material by an impulse means;

connecting a force transducer to the impulse means;

detecting by a vibration sensor a response signal in the material as a result of the impulse imparted;

transforming the response signal into a frequency domain by an analyzer connected to the vibration sensor;

obtaining resonance frequencies of the plate from the analyzer;

deriving modal shape indices of the plate at each resonance frequency;

communicating the resonance frequencies and the modal shape indices to a computing means;

computing and displaying ($E_x$, $E_y$, $G_{xy}$, and $v_{xy}$) four elastic constants using the computing means; and determining after the computing and displaying step that the material is orthotropic or isotropic by inspection of the four elastic constants.

3. The method of claim 1 wherein the step of suspending the material comprises suspending an orthotropic material.

4. The method of claim 1 wherein the step of suspending the material comprises suspending an isotropic material.

5. The method of claim 1 wherein the step of suspending the material comprises suspending an aluminum material.

6. The method of claim 1 wherein the step of suspending the material comprises suspending a graphite/epoxy material.

7. The method of claim 1 wherein the step of suspending the material comprises suspending a glass/vinylester material.

8. An apparatus for determining the elastic properties of a panel of a thin composite material non-destructively, comprising:

a rigid support;

a fine suspending medium extending from the support, the suspending medium having a low support stiffness, thereby engaging the material so that edges of the material are essentially free of restraint by the suspending medium;

an impulse means for imparting an impulse to the material;

a force transducer connected to the impulse means;

a vibration sensor for detecting the response in the material as a result of the impulse imparted and for generating a signal in proportion thereto;

a spectrum analyzer connected to the vibration sensor for transforming the signal into a frequency domain and obtaining resonance frequencies and modal shape indices of the panel;

a computing means in communication with the analyzer for computing from the resonance frequencies and the modal shape indices, all four elastic constants and for displaying said constants so that a determination can be made that the material is orthotropic or isotropic;

the rigid support including:
a vibration isolation table;
a support stand rigidly connected to the vibration isolation table;
a cross-piece extending from the stand, the cross-piece having opposite ends;
two cantilever bars, one bar being clamped to one end of the cross-piece, and the other bar being clamped to the other end of the cross-piece.

9. The apparatus of claim 8 wherein the suspending medium extends downwardly from the cantilever bars.

* * * * *

UNITED STATES PATENT AND TRADEMARK OFFICE
CERTIFICATE OF CORRECTION

PATENT NO. : 5,533,399
DATED : July 9, 1996
INVENTOR(S) : Emmanuel O. Ayorinde and Ronald F. Gibson It is certified that error appears in the above-indentified patent and that said Letters Patent is hereby corrected as shown below:

On the title page, under item [19], change "Gibson" to --Ayorinde--, item [75], should read --Emmanuel O. Ayorinde and Ronald F. Gibson--.

Title page, column 2, line 4, "Floria" should be --Florida--.

Title page, column 2, line 10, "Came" should be --Carne--.

Column 5, line 1, equation (8), the "minus" signs after small "c" and small "d" respectively should be --=-- signs.

Column 5, line 1, "$E_{ij}-E_{ij}$", first occurrence, should be --$E_{ij}-E_{ji}$--.

Column 5, line 66, equation (18) the "-" sign should be --=--.

Column 7, line 23, equation (25), the "-" sign should be --=--.

Column 7, line 33, "$C_b$" (second occurrence) should be --$C_h$--.

Column 9, line 14, "$(E_x/E_y)^{\frac{1}{4}}$" should be --$(E_x/E_y)^{\frac{1}{2}}$--.

Column 9, line 59, after "and" and before "were" insert --v--.

Signed and Sealed this

Twenty-sixth Day of November 1996

Attest:

BRUCE LEHMAN

Attesting Officer     Commissioner of Patents and Trademarks